(12) United States Patent
Dong et al.

(10) Patent No.: US 7,520,994 B2
(45) Date of Patent: Apr. 21, 2009

(54) METHOD TO REMOVE AGENT FROM LIQUID PHASE

(76) Inventors: Xing Dong, 715 Mansion Cir., Apt. E, Chattanooga, TN (US) 37405; Henry Paris, 1111 Valentine Cir., Chattanooga, TN (US) 37405

( * ) Notice: Subject to any disclaimer, the term of this patent is extended or adjusted under 35 U.S.C. 154(b) by 0 days.

(21) Appl. No.: 11/777,082

(22) Filed: Jul. 12, 2007

(65) Prior Publication Data

US 2008/0011683 A1    Jan. 17, 2008

Related U.S. Application Data

(60) Provisional application No. 60/807,151, filed on Jul. 12, 2006.

(51) Int. Cl.
*C02F 1/42* (2006.01)

(52) U.S. Cl. .................... 210/661; 210/670; 210/688; 210/695

(58) Field of Classification Search ................. 210/661, 210/670, 688, 695
See application file for complete search history.

(56) References Cited

U.S. PATENT DOCUMENTS

| | | | |
|---|---|---|---|
| 4,010,239 A | 3/1977 | Dor | |
| 4,144,373 A | 3/1979 | Weiss et al. | |
| 4,177,253 A | 12/1979 | Davies et al. | |
| 4,201,831 A | 5/1980 | Slusarczuk et al. | |
| 4,652,533 A | 3/1987 | Jolley | |
| 4,672,040 A | 6/1987 | Josephson | |
| 4,698,302 A * | 10/1987 | Whitehead et al. | ............ 435/94 |
| 4,824,576 A | 4/1989 | Sood et al. | |
| 5,098,684 A | 3/1992 | Kresge et al. | |
| 5,102,643 A | 4/1992 | Kresge et al. | |
| 5,238,676 A | 8/1993 | Roth et al. | |
| 5,264,203 A | 11/1993 | Beck et al. | |
| 5,279,936 A | 1/1994 | Vorpahl | |
| 5,384,106 A | 1/1995 | Johnson | |
| 6,045,700 A | 4/2000 | Heitkamp et al. | |
| 6,103,127 A | 8/2000 | Pourfarzaneh | |
| 6,326,326 B1 | 12/2001 | Feng et al. | |
| 6,416,671 B1 * | 7/2002 | Pourfarzaneh | ............... 210/690 |
| 6,521,021 B1 | 2/2003 | Pennline et al. | |
| 6,531,224 B1 | 3/2003 | Fryxell et al. | |
| 6,541,539 B1 | 4/2003 | Yang et al. | |
| 6,592,764 B1 | 7/2003 | Stucky et al. | |

(Continued)

OTHER PUBLICATIONS

Aoyama et al., Chemical Adsorption of Silazane on Magnetic Iron Oxide, The American Ceramic Society (199) pp. 273-279, vol. IV.

(Continued)

*Primary Examiner*—Chester T Barry
(74) *Attorney, Agent, or Firm*—Baker, Donelson, Bearman, Caldwell & Berkowitz, PC

(57) ABSTRACT

A system and method to remove a polluting agent or contaminant, including but not limited to mercury, from the liquid phase of a process system using an adsorbent. In one exemplary embodiment, a magnetic or non-magnetic support with a chemisorbing or physisorbing sorbent is suspended in the liquid phase of a process system, under conditions in which the polluting agent binds to the adsorbent. The pollutant-bearing adsorbent may then be separated from the process system by either physical or magnetic means. The polluting agent may then disassociated from the adsorbent so the adsorbent is regenerated and capable of repeated use.

12 Claims, 11 Drawing Sheets

U.S. PATENT DOCUMENTS

| | | | |
|---|---|---|---|
| 6,596,182 | B1 | 7/2003 | Prenger et al. |
| 6,695,894 | B2 | 2/2004 | Chang et al. |
| 6,706,097 | B2 | 3/2004 | Zornes |
| 6,712,878 | B2 | 3/2004 | Chang et al. |
| 6,716,378 | B2 | 4/2004 | Yang et al. |
| 6,733,835 | B2 | 5/2004 | Fryxell et al. |
| 6,746,767 | B2 | 6/2004 | Gottfried et al. |
| 6,753,038 | B2 | 6/2004 | Fryxell et al. |
| 6,787,307 | B1 | 9/2004 | Bitner et al. |
| 6,846,554 | B2 | 1/2005 | Fryxell et al. |
| 2003/0159996 | A1 | 8/2003 | Ernst |
| 2005/0025690 | A1 | 2/2005 | Kentaro et al. |
| 2005/0155934 | A1* | 7/2005 | Vo et al. ............ 210/670 |
| 2006/0207942 | A1 | 9/2006 | Yang |
| 2008/0071129 | A1* | 3/2008 | Yang et al. ............ 588/301 |

OTHER PUBLICATIONS

Aoyama et al., Adsorption of silane coupling agent on Co-y-Fe2O3 and its effect on dispersibility, Journal of Materials Science 23 (1988) 1729-1734.

Bodziony et al., Low Concentration Effect of Fe3O4 and Fe3C Magnetic Nanoparticles in Non-Magnetic Matrix on the FMR Spectra, ACTA Physica Polonica A, vol. 108 (2005) pp. 297-302.

Bromberg et al., Nerve Agent Destruction by Recyclable Catalytic Magnetic Nanoparticles, Ind. Eng. Chem. Res. 2005, 44, 7991-7998.

Feng et al., Self-Assembled Mercaptan on Mesoporous Silica (SAMMS) Technology for Mercury Removal and Stabilization, Sep. 1997, prepared for the U.S. Department of Energy, Pacific Northwest National Laboratory, Richland, Washington.

Ghebremeskel et al., Magnetic colloid mediated recovery of cadmium ions from an aqueous solution using a flow-through hybrid field-gradient device, Separation Science and Technology, vol. 37 (2002) pp. 555-569.

Grun et al., Novel pathways for the preparation of mesoporous MCM-41 materials: control of porosity and morphology, Microporous and Mesoporous Materials 27 (1999) 207-216.

Jal et al., Chemical modification of silica surface by immobilization of functional groups for extractive concentration of metal ions, Talanta 62 (2004) 1005-1028, available online at www.sciencedirect.com.

Lee et al., Synthesis of thiol functionalized organo-ceramic adsorbent by sol-gel technology, Reactive & Functional Polymers 49 (2001) 159-172.

Lin et al., Aqueous Free Radically Chemistry of Mercury in the Presence of Iron Oxides and Ambient Aerosol, Pergamon, Atmospheric Enviornment vol. 31, No. 24, pp. 4125-4137, 1997.

Liu et al., Further investigations on the modified Stober method for spherical MCM-41, Materials Chemistry and Physics 97 (2006) 203-206.

Merrifield et al., Uptake of mercury by thiol-grafted chitosan gel beads, Walter Research 38 (2004) 3132-3138.

Mou et al., Control of morphology in synthesizing mesoporous silica, Pure Appl. Chem., vol. 72, Nos. 1-2 pp. 137-146, 2000.

Olkhovyk et al., Ordered Mesoporous Silicas with 2,5-Dimercapto-1,3,4-Thiadiazole Ligand: High Capacity Adsorbents for Mercury Ions, Springer Science & Business Media, Inc., Adsorption 11: 205-214, 2005.

Perez-Quintanilla et al., 2-Mercaptothiazoline modified mesoporous silica for mercury removal from aqueous media, Journal of Hazardous Material-5136 (2005).

Shin et al., Supercritical processing of functionalized size selective microporous materials, Microporous and Mesoporous Materials 37 (2000) 49-56.

Tsang et al., Novel Magnetic Separable Nano-Carriers for Chemical Catalysis & Bio-Catalysis, NSTI-Nanotech 2005, www.nsti.org, ISBN 0-9767985-1-4 vol. 2, 2005, pp. 615-618.

Weinstein et al., Self-Assembled Monolayer Films from Liquid and Supercritical Carbon Dioxide, Materials and Interfaces, Ind. Eng. Chem. Res. 2001, 40, 2046-2053.

Innovative Technology Shows Promise for Low-Cost Mercury Control—Patented DOE Process Licensed to Industry for Commercial Development, Fossil Energy Techline Office of Communications (Jun. 2, 2005) found at http://www.fossil.energy.gov/news/techlines/2005/tl_thief_process.html.

Mercury Emission Control R&D, Fossil Energy Office of Communications (updated Jan. 18, 2006) at http://www.fossil.energy.gov/programs/powersystems/pollutioncontrols/overview_mercurycontrols.html.

The Need for Additional U.S. Coal-Fired Power Plants (Release date Jul. 5, 2005) available at http://www.asme.org/NewsPublicPolicy/GovRelations/PositionStatement/Need_Additional_CoalFired.com.

U.S. Enviornmental Protection Agency, 1997, Mercury Study Report to Congres. vol. VIII: An Evaluation of Mercury Control Technologies and Costs. Office of Air Quality Planning and Standards, Dec. 1997.

Nunez et al., Transuranic Separation Using Organophophorus Extracts Adsorbed Onto Superparamagnetic Carriers, Journal of Magnetism and Magnetic Materials (JMMM) Conference Proceedings, May 28-30, 1998, Work supported by the U.S. Department of Energy under contract W-31-109-ENG-38.

* cited by examiner

METHOD TO REMOVE AGENT FROM LIQUID PHASE

This application claims benefit of, and priority to, U.S. Provisional Patent Application No. 60/807,151, filed Jul. 12, 2006, entitled "METHOD TO REMOVE AGENTS USING AN ADSORBENT ATTACHED TO A SUPPORT FROM THE LIQUID PHASE OF A PROCESS SYSTEM." The specification, drawings, and complete disclosure of U.S. Provisional Patent Application No. 60/807,151 are incorporated herein by specific reference.

TECHNICAL FIELD

The present invention relates to the removal of an agent, such as mercury, from process systems, such as a waste stream comprising an aqueous or organic liquid. More particularly, the present invention relates to the removal of an agent from the liquid phase of a process system using an adsorbent comprising a sorbent attached to a support.

BACKGROUND OF THE INVENTION

Mercury is an impurity at low concentration in the earth's crust. Mercury is present in three basic forms: metallic; inorganic mercury in $Hg^{+1}$ or $Hg^{+2}$ valence states (e.g., as an inorganic chloride); and organic mercury bound to phenyl-, alkoxyalkll-, or methyl-groups. Methyl mercury and elemental mercury are the most hazardous forms.

Major sources of mercury pollution include impurities in or contamination of industrial processes, such as gaseous effluent from burned coal and from chlor-alkali plants that can become entrained in liquid process streams such as from wet scrubbers, as well as liquid effluent from industrial processes, such as mining operations and crude oil drilling. Another source is accidental release.

Coal forms by the combination of long-term putrefaction and pressurization under reducing conditions of prehistoric buried organic plant matter. Given the nature of the natural process that makes coal and the high solubility of mercury in organic solvents, mercury often finds its way into coal. The solubility of mercury in benzene, heptane, isopropyl ether, and iso-octane is between approximately 1 to 2.5 mg/l. Its solubility in water is approximately 0.064 mg/l. While mercury exists in very small concentrations in coal, the massive volume of coal burned for power generation yields a significant (i.e., 40% or greater) overall emission of mercury into the environment.

The two prevalent classifications of coal are bituminous and brown (i.e., lignite or sub-bituminous). Bituminous coal from the eastern U.S. contains primarily ionic mercury. Sub-bituminous coal, mainly from the western U.S., yields predominately elemental mercury. Sub-bituminous coal, which contains mercury in a more hazardous form, is the predominant source of coal.

Because of the two types of coals and the characteristics of specific power plants, the boiler in a typical power plant releases mercury in both forms, ionic and elemental. Downstream wet scrubbers more readily remove the ionic form, thereby creating a liquid process stream containing mercury. The elemental form of mercury is more difficult to remove from the gas stream. Most methods to remove mercury in the gas phase aim to convert all the mercury to an ionic form. Unless the effluent of the wet scrubber contains substances that bind the ionic mercury (e.g., sulfate anions), the effluent water will be contaminated with the mercury removed from the gaseous state.

Mercury may also be released into the environment in soluble forms when it has been oxidized and/or converted to a soluble salt, such as a chloride, or organic forms such as methyl mercury. These forms may be soluble in organic or aqueous liquids.

The Electric Power Research Institute (EPRI) has examined a number of approaches to mercury removal from flue gas. The steps in the power plant generation cycle involve feeding coal to the combustor, combustion of coal, collection of flue gas, removal of $NO_X$ and particulates, removal of $SO_X$, and exhaust to the environment. The complicating factor in this cycle is that coal-fired power plants are of varying age, and some have only part of the pollution abatement methods described below (or in some cases, none at all), depending on age and location. The pollution abatement methods described below address removal of the contaminant from the waste stream from the combustion of coal. The waste stream comprises $NO_X$, $SO_X$, coarse ash, fine fly ash, $CO_2$ and mercury.

An important consideration is how removal of mercury impacts the quality of fly ash and gypsum (calcium sulfate from $SO_X$ removal). Primary markets for fly ash and gypsum are as a substitute for cement in concrete, and from gypsum as wallboard and soil amendments. If mercury is bound to fly ash or enters the $SO_X$ scrubbers it may ruin the use of these components in these applications.

Known methods to remove mercury from waste streams are as follows:

Coal Cleaning. Bituminous coal is cleaned routinely prior to combustion to remove non-combustibles. Although not intended for the purpose, this cleaning removes up to approximately 35% of the mercury. EPRI states it is unlikely to achieve a higher reduction in mercury in bituminous coal by cleaning. In contrast, sub-bituminous coal is usually not cleaned. De-watering processes under development for sub-bituminous coal may have the potential to remove up to approximately 70% of the mercury.

Additives To Oxidize Mercury. An oxidizer (e.g., salts, such as chloride) may be added to oxidize the mercury and convert it to ionic form. This makes the mercury more susceptible to removal by scrubbers and other methods described herein, which remove mercury in ionic form.

Modify the Combustion Process. Activated carbon is effective to remove mercury. Increasing the content of un-oxidized carbon in the flue gas by modifying the combustion process enhances removal of the mercury in this manner. However, the mercury-laden particulate in the fly ash renders the fly ash unusable. Changing the oxidation/reduction character of the combustion process also leads to lower efficiency.

Selective Catalytic Reduction (SCR). Another approach oxidizes mercury in the SCR (which converts $NO_X$). Downstream wet scrubbers collect the oxidized mercury in an aqueous stream. An alternate approach uses a mercury-selective catalyst in the gas stream for this purpose. Typically this involves a "fixed absorbent structure" with plates or channels lined with the adsorbents such as gold, sulfur or activated carbon. A major issue with SCR for oxidation for mercury is whether such devices can maintain selective oxidative power over a reasonable life, i.e., approximately 12,000-16,000 hours (12-22 months), and whether sufficient contacting of adsorbent with mercury can be achieved.

Sorbent Injection. Activated carbon is a very good adsorbent of mercury. However, the cost of activated carbon is a significant issue. An EPRI publication cites short-term tests that removed up to 80-85% of mercury from bituminous coal fired plant operations by injecting activated carbon as a fine powder in the flue gas. However, the removal of mercury in western coals peaks at 65-70%. This method requires injection of a sizable quantity of expensive carbon "dust." A further complication of using this method, or any method that injects activated carbon upstream, is that the carbon with adsorbed mercury contaminates the collected ash in the latter stages of the flue gas cleaning process, rendering the fly ash commercially useless for the largest current application (i.e., as a substitute for cement in concrete). This method thus may require an additional step of removal of the mercury from the ash, such as using sulfur-added (or bromine-added) activated carbon. The efficiency of this additional step is debatable. The durability of the injection process also is not well known and is an area of active development. The necessity to control location of the activated carbon injection into the waste steam to avoid contaminating the fly ash with mercury is a disadvantage. The carbon might be injected after the electrostatic precipitator (ESP) to avoid contaminating the fly ash, but this still requires a "polishing" fabric filter to remove the carbon holding the captured mercury. The filters, however, may increase back pressure of the flue. While some polishing filters being tested report 85-95% efficiency in short term tests, full scale, long term tests have not been completed.

Electrostatic Precipitators. The ESP is virtually useless for removing mercury unless some upstream process is used to bind mercury to particulates, such as, for example, activated carbon injection. Typical efficiency for mercury removal is from 0% to approximately 35% for ESP without particulate binding. The efficiency of the process using fabric filters increases removal to approximately 35-99% for bituminous coal and approximately 48-86% for sub-bituminous coal. When sorbents are used, ESP with fabric filters leads to mercury in the fly ash. As mentioned previously, this contaminates the fly ash.

FGD (Flue Gas Desulphurization) Additives and Scrubbers. This developing technology injects active material into the liquid in the $SO_X$ scrubbers, which remove $SO_X$, primarily as sulfate. The additive reacts with the mercury to form non-volatile salts. The reaction must be fast enough to avoid contaminating the calcium sulfate that forms in reaction with the slurried limestone, and thus prevent contamination of the resultant gypsum. FGD will remove approximately 90-95% of ionic mercury, but little or no elemental mercury.

Fixed Absorption Structure. In this developing technology, plates or honeycomb structures with mercury-adsorbent materials, such as gold or activated carbon, are placed in the flue gas stream.

These prior art methods are not completely satisfactory for removing mercury because conventional adsorbents, such as activated carbon, sulfur and elemental gold, each have particular problems, including but not limited to expense, contaminating the fly ash, and related performance issues even when they demonstrate high efficiency at removing mercury from the gas stream. The main reason appears to be that the specific adsorbents work only, or best, with mercury in its oxidized state and do not work very well in its unoxidized or elemental vapor state. Another undesirable characteristic of activated carbon is that mercury is typically physically adsorbed (physisorbed) to it, not chemically adsorbed (chemisorbed). This means the mercury is not strongly bound and may be removed by physical actions such as washing or contacting the activated carbon with a mildly reactive chemical, thus making the activated carbon a potential hazard.

Another industrial source of mercury contamination are chlor-alkali plants that use liquid mercury in an electrochemical process to produce sodium hydroxide and chlorine. These have the potential of mercury in process streams. Mercury concentration in the air on roads adjacent to two chlor-alkali plants has been reported at 1,788 ng/m$^3$ and 2,629 ng/m$^3$, both being far above the EPA reference concentration for chronic mercury exposure of 300 ng/m$^3$ and the Agency for Toxic Substances and Disease Registry (ATSDR) safe level for chronic exposure of 200 ng/m$^3$. The EPA states that the most significant potential emission point in chlor-alakli plants is thought to be the Hg cell building roof vent. This implies a primary source is gaseous mercury. Although these reports suggest most of the mercury is emitted in gaseous form, it may become part of a liquid stream in the plant, or in the run-off of water in the general area adjacent to the plant where high air concentrations of mercury are found.

Sulfide precipitation appears to be the common practice for mercury control in many chlor-alkali plants, and achieves levels of 95-99.9% reduction for well-designed and managed treatment. Such methods typically use sodium hydrosulfide or magnesium sulfide to form a relatively insoluble mercury sulfide, HgS, which precipitates and forms a sludge. Studies have cited examples where initial levels of 10 ppm (10 mg/L) are reduced to 10-100 ppb (10-100 µg/L). However for effect, these processes must work at a pH less than 9. This type of treatment creates significant mercury-laden sludge that in itself is a potential environmental hazard if placed in landfill because it may create mercury leachate and ground-water pollution. In addition, this sulfide precipitation method appears not to be able to reduce mercury below 10-100 ppb (10-100 µg/L).

In a separate report from Oak Ridge National Laboratory, mercury concentration in wastewater varied between 105 to 837 ng/liter (parts per trillion, ppt) while the EPA requirement is no more than 19 ppt. Thus, industrial operations may yield mercury pollution in both aqueous and gaseous state. The report described a variety of other remediation methods, including other precipitation methods, although these were not substantial improvements over sulfide precipitation. Included in these other remediation methods were adsorption processes using activated carbon in either granular form (GAC) or powder form (PAC). These methods used filter beds and a micro-filtration process to capture lost activated carbon containing mercury. The best method using a 10 ppm (10 mg/L) input achieved an output mercury concentration of approximately 0.2-1.0 ppb (0.2-1.0 µg/L). To achieve such low levels, PAC is soaked in $CS_2$ and filtered. The performance is attributed to chemisorbed mercury to the $CS_2$. The study suggested that adsorption using activated carbon drops as the solution pH deviates much from 4-5. A major drawback of this approach is that the activated carbon cannot be regenerated economically. In addition, the carbon works by the principle of physisorbing the mercury or the $CS_2$. This means that the carbon has the same problem as sludge from precipitation. If it is disposed the potential for leaching and ground-water pollution cannot be ignored.

While ion exchange methods, at least on bench scale, can achieve 0.4-1 ppb (0.4-1 µg/L) final concentrations, they cannot be used in aqueous streams with high solids content, create mercury-contaminated brine when regenerated, and can exhibit substantial variability. These methods rely on the exchange of the mercury cation in a soluble form, and thus they work mostly in high chlorine streams.

A variation of the precipitation method uses small magnetic particles to act as nucleation sites for a coagulation or precipitation reaction involving the mercury. These mercury-laden precipitates are filtered from the stream. For an input concentration of 15 mg/L, this method on the bench scale reported a final concentration of mercury of 3 ppB (µg/L) to 0.117 ppm (mg/L) when used on a waste stream of a municipal solid waste incinerator. These precipitates have similar problems as previous methods: they pose disposal problems and do not demonstrate very low final mercury levels.

Accordingly, what is needed is a method of removal of a contaminant such as mercury from process streams that avoids the shortcomings of the known methods described above. In particular, an adsorbent method is needed that allows for more and longer contacts of the adsorbent surface with the contaminant, and that strongly chemisorbs the contaminant so it does not leach or readily regenerate the mercury. It is to such that the present invention is directed.

SUMMARY OF THE INVENTION

This invention is directed to a system and method to remove a polluting agent or contaminant, including but not limited to mercury, from the liquid phase of a process system using an adsorbent. The adsorbent may comprise a sorbent on a support or substrate. In one exemplary embodiment, a magnetic or non-magnetic support of a chemisorbing or physisorbing small sorbent is suspended in the liquid phase of a process system, under conditions in which the polluting agent binds to the adsorbent. The pollutant-bearing adsorbent may then be separated from the process system by either physical or magnetic means. The polluting agent may then disassociated from the adsorbent so the adsorbent is regenerated and capable of repeated use.

In one exemplary embodiment, the wetting character of the adsorbent may be modified so as to enhance its use in either organic or aqueous liquids. A filter material may be used, the filter material comprising an adsorbent by itself or in combination with a media that holds and suspends adsorbent so it has free contact with the liquid. The adsorbent may comprise a support, such as, but not limited to, silica, and an adsorbent chemical moiety that exhibits strong chemical bonding to the pollutant.

The present method and system may be used to remove the polluting agent from the liquid effluent and waste stream generated during a chemical process, such as, but not limited to, the operation of mercury-containing diffusion pumps, the manufacture of fissionable materials for weapons or nuclear power, or the operation of coal-fired electricity generating plants. The method uses a magnetic or non-magnetic carrier of a small sorbent whose wetting character in organic and aqueous liquids can be controlled, a collection system for the spent adsorbent and a regenerating method for the spent adsorbent. While the aforementioned installations are but several examples, the method of the present invention will find particular application to the removal of mercury from an aqueous or liquid waste stream containing mercury produced by such installations as a coal-fired utility plant or a crude oil well. Other such processes could include incineration plants, landfills, waste-to-energy plants, chlor-alkali plants, oil fields producing crude oil or natural gas, or any other industrial processes which generate liquid containing mercury or gaseous products that contain mercury that becomes dissolved in a liquid.

In one exemplary embodiment, a mixture of process stream and adsorbent is stirred or circulated for some period of time to maximize contact and chemical binding of pollutant such as mercury in the process stream. The solids-to-liquid ratio, and the time the adsorbent is maintained in contact with the solution, may be adjusted depending on the starting concentration of mercury, the desired terminal concentration, and the residence time. The amount of contacting of the adsorbent and mercury-containing liquid is controlled by the total time of filling, mixing and draining of the container holding the process stream and adsorbent, and by the rate of binding of mercury to the adsorbent. After the desired period of time, the process stream liquid is pumped from the tank through a filter to remove from the process stream the adsorbent with bound mercury. The filling time of the tank can be adjusted to match the rate of removal of mercury determined by the adsorption kinetics of the adsorbent.

In an alternative embodiment, the process stream is held in the contacting tank with stirred or circulating adsorbent for the time required to reduce the concentration of the polluting agent to the desired terminal concentration. At this time, an array of soft-magnetic metal electromagnets or hard magnets is inserted into the circulating liquid in the container vessel to attract and remove the adsorbent particles from the liquid. The suitable time to hold the magnetic array in the liquid to collect all the adsorbent may be determined by the magnetic moment of the support particle, the amount of fluid circulation, and experience. The term "electromagnet" is used, but a permanent magnetic solution can also be used by slightly modifying the magnetic separator construction. After a suitable time of energizing the electromagnet array in the circulating fluid to collect the adsorbent on the magnetic array, the fluid is pumped from the contacting vessel and placed in a second receiving vessel or into the process stream. It may be beneficial to have a filter in the exhaust line for the process stream to capture any residual adsorbent that has not been captured by the electromagnetic removal system.

If the adsorbing capacity of the adsorbent is quite high, the treatment of a single batch of process fluid may not exhaust its adsorbing capacity. In this embodiment, it may be preferable to keep the electromagnetic array energized to hold the adsorbent while the tank is drained. Then new process fluid can be pumped into the contacting vessel and the electromagnet array de-energized to release the adsorbent particles. The stirring or circulating mechanism is then turned on and the cycle begins anew.

In one exemplary embodiment, the contacting vessel can be modified with piping to permit samples to be obtained of the process stream from the contacting tank. This piping can be connected to a chemical sensing system to monitor the concentration of mercury or polluting agent and to follow the adsorption process. Samples of the adsorbent may be obtained from the electromagnetic removal system to determine the activity of the adsorbent. If desired, when the adsorbent on the magnetic carrier has reached its acceptable state of capacity of mercury, the electromagnetic removal system may remove adsorbent from the vessel so it may be disposed of.

It may be desirable to regenerate the adsorbent by removing the mercury when the adsorbent has reached its acceptable state of capacity. In one exemplary embodiment, this may be accomplished by pumping into the empty contacting tank a liquid with a strongly acidic character (e.g., of pH about 1 or below). An example of such a liquid is 37% (by weight) hydrochloric acid. The acid removes the mercury from the adsorbent, thereby regenerating the adsorbent and leaving the mercury in the solution as a chloride salt. The fluid containing the removed mercury salt may be removed by pumping, leaving the regenerated adsorbent in the tank for a new cycle.

In some embodiments where space for the adsorbing apparatus is limited, it may be advantageous to replace the contacting tank and other equipment with a series of in-line filters that achieve the same contact time between the adsorbent and process stream. This may be required if space allows replacement of a run of existing piping but not enough space for a suitably-sized contacting tank.

A combination of a bank of filters and a contacting tank also may be used. In this configuration, it may be desired to remove the adsorbent by physical separation rather than electromagnetic separation. In such cases, the first receiving vessel contains suitable pumps, piping and valves to move the liquid of the process stream through a filter medium to remove the mercury-containing adsorbent. A special filter medium is used that traps the adsorbent particulate. This filter medium may be constructed of a fibrous material that is readily made into a non-woven or woven configuration to provide small passages which will trap the adsorbent particulate as it moves through the filter medium. Suitable consideration will lead one to fabricate this non-woven or woven material with a passage size, and perhaps a density of passage sizes, to allow systematic capture of adsorbent particles and other detritus in the liquid in a controlled manner to enhance filter life and total capture capability.

In another embodiment of the present invention, after the process stream with reduced pollutants is removed, piping and valves may be actuated to run a cleansing liquid back through the filters (in an action called "back flushing") that moves the adsorbent back into the contacting tank. A new batch of incoming process stream could be used to back flush so as to begin the cycle of removing mercury from the process steam.

In yet another embodiment, the filter medium may be constructed of a material that can be dissolved or decomposed in a second liquid, so as to release the adsorbent particles and other detritus removed from the original agent-contaminated process stream. At this point, a magnetic separator may be used to capture the adsorbent particles from the dissolving liquid, and subject them to the regeneration procedure for re-use. An example of such material for a filter medium is cellulose acetate, which is used as the filter on tobacco cigarettes. A suitable solvent for the cellulose acetate filter medium is the organic solvent acetone. Other combinations of materials and solvent can also be used.

The invention does not require recovery of the agent from the soluble filter medium. It may be desirable to simply dispose of the filter medium containing the adsorbent holding the chemisorbed agent in a suitable disposal site such as a land fill. In such a case, for example, a mercury-contaminated liquid in the original holding vessel that has had the mercury concentration reduced to the desired level is removed by admitting a source of cleansing liquid into the filter medium flowing back into the original holding tank. This liquid flushes any physically adsorbed mercury from the adsorbent. The chemisorbed mercury is not removed. The liquid goes back into the original holding tank where it becomes part of the new batch of liquid contaminated with mercury for the subsequent cleaning steps as described above. The flushed filter medium now only holding primarily chemisorbed mercury can be removed and cleaned of the agent as previously described. These steps may be repeated as necessary to achieve a desired final concentration of the mercury in the waste stream and to recover bound mercury in adsorbent.

In an alternative embodiment, the filter medium may be designed to be highly acid resistant so as to allow, after filtering the mercury, a similar flushing operation using 12 N HCL to remove the mercury back into the contacting tank where it can be recovered and concentrated into a form for subsequent use of disposal.

Embodiments of the present invention have inherent advantages over the prior art that improve how a polluting agent is removed from a liquid stream. The present invention provides a regenerable and recyclable chemisorbing or physisorbing small adsorbent species, attached to a substrate or otherwise able to be separated from the liquid exhaust stream. It offers a direct way to mix and recover pollutants, and a direct and effective way to strongly bind the pollutant to an adsorbent so it may be disposed of without potential for leaching. The adsorbent may be regenerated and reused if desired, and the adsorbent provides a higher capacity for adsorption and faster kinetics, allowing improved efficiency of the filtration process. The method also can use existing filtration processes and filters. This provides considerable economic advantages that can reduce the cost of removal of the polluting agents. Another advantage is that the present invention, in one exemplary embodiment, works on both oxidized and unoxidized forms of mercury.

Still other advantages of various embodiments will become apparent to those skilled in this art from the following description wherein there is shown and described exemplary embodiments of this invention simply for the purposes of illustration. As will be realized, the invention is capable of other different aspects and embodiments without departing from the scope of the invention. Accordingly, the advantages, drawings, and descriptions are illustrative in nature and not restrictive in nature.

DETAILED DESCRIPTION OF EXEMPLARY EMBODIMENTS

Figure 1:
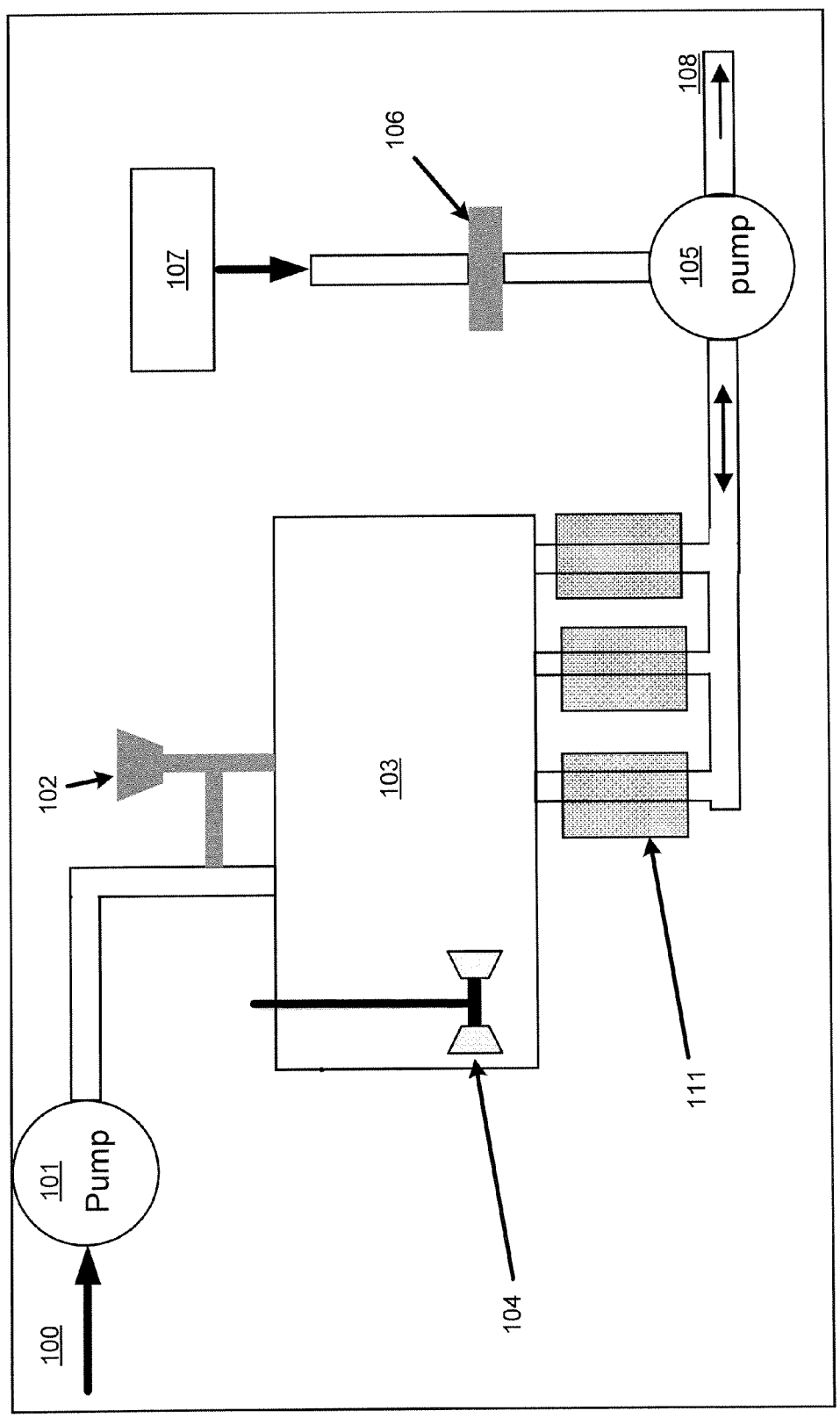
FIG. 1 is a diagram of a process in accordance with an exemplary embodiment of the present invention.

FIG. 1 illustrates a separating system to remove a polluting agent, including, but not limited to, mercury, from a liquid waste stream 100 by means of an adsorbent 102. The adsorbent 102 may be collected, regenerated and reused. The liquid effluent and waste stream 100 may be generated during a chemical process, such as, but not limited to, the operation of mercury-containing diffusion pumps, the manufacture of fissionable materials for weapons or nuclear power, or the operation of coal-fired electricity generating plants. Other such processes could include incineration plants, landfills, waste-to-energy plants, chlor-alkali plants, oil fields producing crude oil or natural gas, or any other industrial processes which generate liquid containing mercury or gaseous products that contain mercury that becomes dissolved in a liquid. Thus for the sake of convenience, the terms gas, industrial gas, or flue gas, and waste stream, liquid waste stream, or liquid will be used herein to refer to any gas or liquid from an industrial process similar to those described herein, including but not limited to a coal-fired utility boiler installation of the type used by utilities in the generation of electric power.

The liquid stream 100 is pumped using a pump 101 into an adsorbent-liquid contacting vessel 103. The contacting vessel 103 also may mix the adsorbent 102 that is being added concurrently with the liquid 100. Such mixing may be enhanced by operation of a mixing device, including but not limited to stirrers, stirring paddles, or recirculation pumps 104. FIG. 1 shows an embodiment using a paddle stirrer 104 for mixing, but any mechanical or hydraulic device or process that mixes liquids and solids may be used.

In one exemplary embodiment, the adsorbent 102 is small and has qualities of chemically adsorbing the pollutant (e.g., mercury). In one embodiment, the adsorbent 102 has binding kinetics that may reduce the concentration of mercury from approximately 10 ppm to less than 1 ppm in less than five minutes. Similarly, one embodiment of the adsorbent 102 may reduce the concentration of mercury to 1 ppb, or lower, in less than 15 minutes. Examples of such adsorbents include, but are not limited to, 3-mercaptopropyl-methoxysilane attached to activated alumina, silica, aluminosilicates, ferrite or others, or ferrites with modified mesoporous surfaces and a high surface density of organo-silicon moieties used to attach suitable adsorbents or catalysts. Such an adsorbent is desirable but the current method is not limited to only this adsorbent.

Figure 6A:
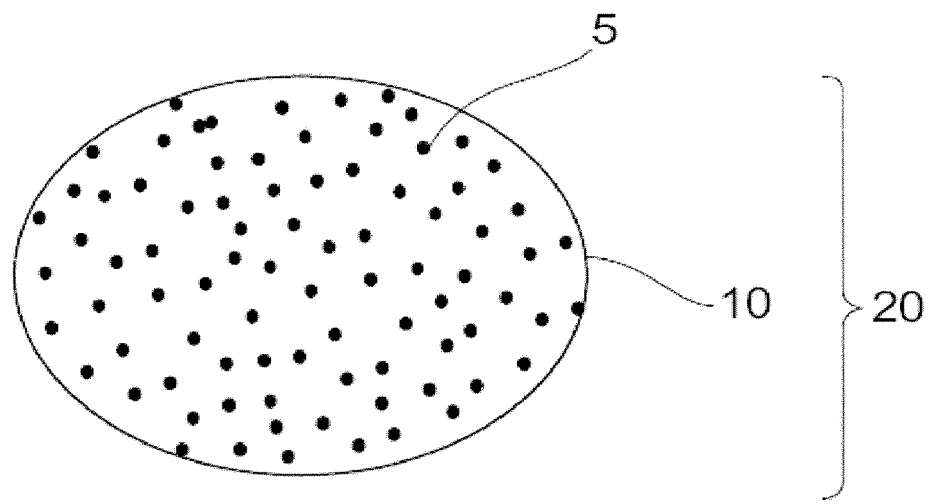
FIG. 6A is a diagram of an adsorbent particle in accordance with an exemplary embodiment of the present invention.

In one exemplary embodiment, the adsorbent 102 comprises a sorbent material 5 on a substrate or support 10. The support may be magnetic or non-magnetic. FIG. 6A shows a sorbent 5, such as a catalyst or adsorbent, attached to a magnetic substrate 10, commonly called the "support." The substrate 10 can be surface modified to provide for attachment points for the sorbent 5. The combination of the magnetic support 10 with a sorbent 5 is referred to a magnetic adsorbent particle or magnetic adsorbent carrier 20. If a non-magnetic support is used, the combination may be referred to as a adsorbent particle or adsorbent carrier. While FIG. 6A illustrates the adsorbent as a particle, a particle form is not required. Other forms include an adsorbent that covers the surface of the support as a discrete discontinuous or continuous monolayer attached to the support surface by chemical, physical or electrostatic bonding.

The support 10 for the adsorbent is preferably of average particle size of about 1 to 100 micrometers, or around 50 micrometers, but may preferably be less than 20 micrometers or 10 micrometers in diameter to increase contact with mercury in solution and accelerate chemical binding. Such porous substrate for the adsorbent will have few or no micropores (pores that smaller than 1-3 nm.) An average pore size may be about 3 nm but preferably 6 nm or larger but less than about 100 nm. The selection of pore size is related to the desire to have a high surface area that has large capacity for the mercury or other agent.

Referring again to FIG. 1, the time from pumping the liquid stream into the tank hold to draining determines the exposure time to reduce the adsorbent to a desired concentration. By using the known concentration of contaminant in the input stream 100, the desired concentration of the purified output stream, the kinetics of adsorption of the contaminant by the adsorbent, and the maximum time the process stream liquid can be held without disrupting upstream processes, the filling time of the tank 103 can be controlled to ensure that sufficient residence time of liquid and adsorbent occur to reach the desired terminal pollutant concentration. After this holding time, a pump 105 drains the liquid from the tank through adsorbent filters 111, resulting in a purified output stream 108. Said filters 111 capture the adsorbent particles but allow the liquid, with the desired percent of pollutant removed, to pass to the output stream 108. When the contacting tank 103 is empty of liquid, the purified output valve 109 is closed and the reverse flow restrictor valve 106 is opened. The pump 105 reverses and pumps liquid from the back-flush liquid source 107 to back-flush liquid through the bank of filters 111. This back-flush liquid moves most of the adsorbent 102 back into the contacting tank 103. The reverse flow restrictor valve 106 may then be closed. Then pump 101 pumps new pollutant-containing process liquid 100 into the contacting tank 103 to begin a new cycle. The process may repeat until the adsorbent filters 111 are laden with sufficient particulate to raise the back pressure to a level requiring the filters to be replaced, or until the adsorbent 102 is at a specified capacity of pollutant.

Figure 2:
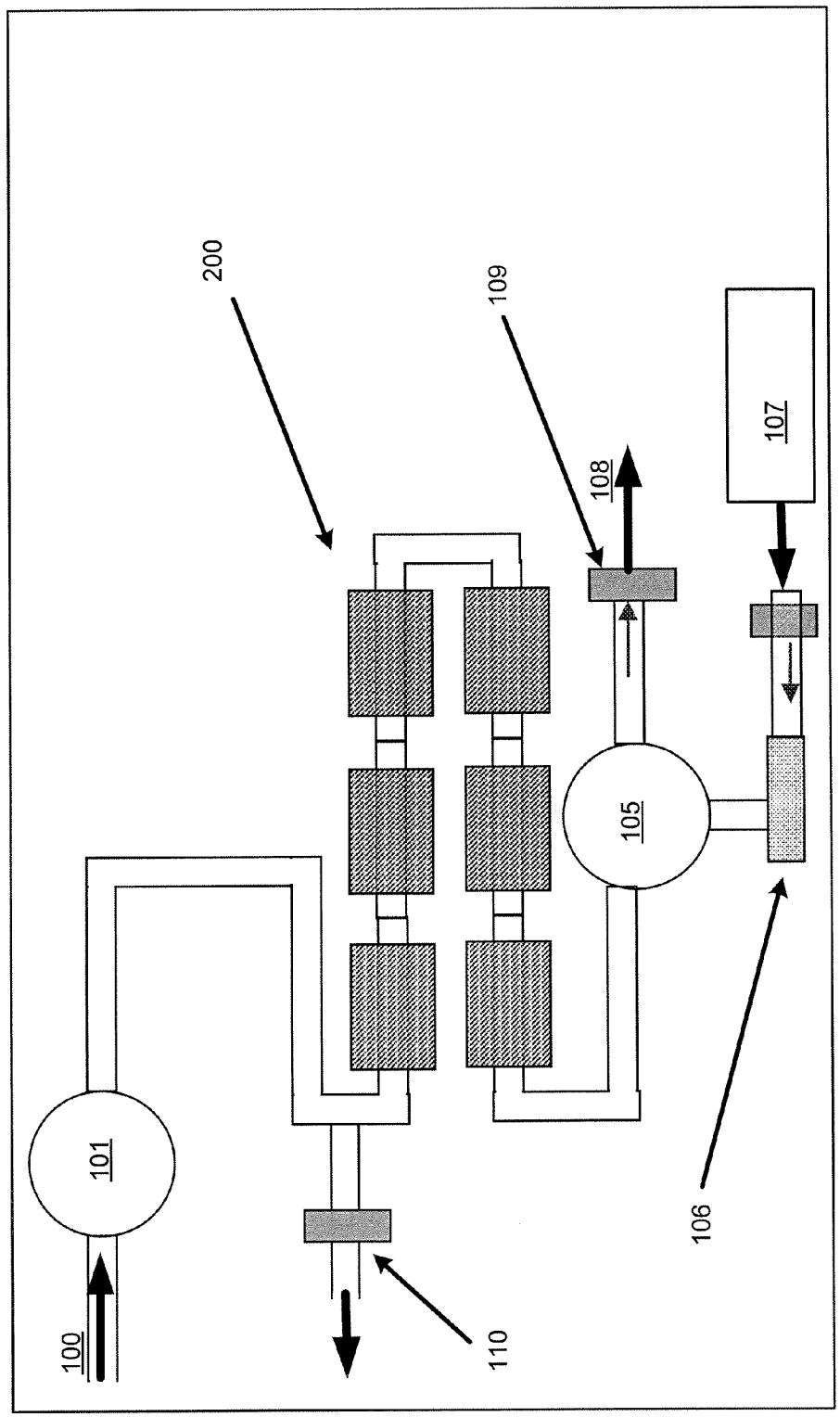
FIG. 2 is a diagram of a process using filter arrays.

FIG. 2 illustrates an alternative embodiment of the system with an in-line filter array 200. This filter array may use the type of filters shown in FIG. 5. This configuration provides advantages in conditions where there is limited space. In another alternative embodiment, designed to allow continuous operation, two sets of in-line adsorbent filter arrays 200 connected in parallel are used with a valve to switch from one bank to the other when necessary (such as when filters need to be replaced).

Figure 3:
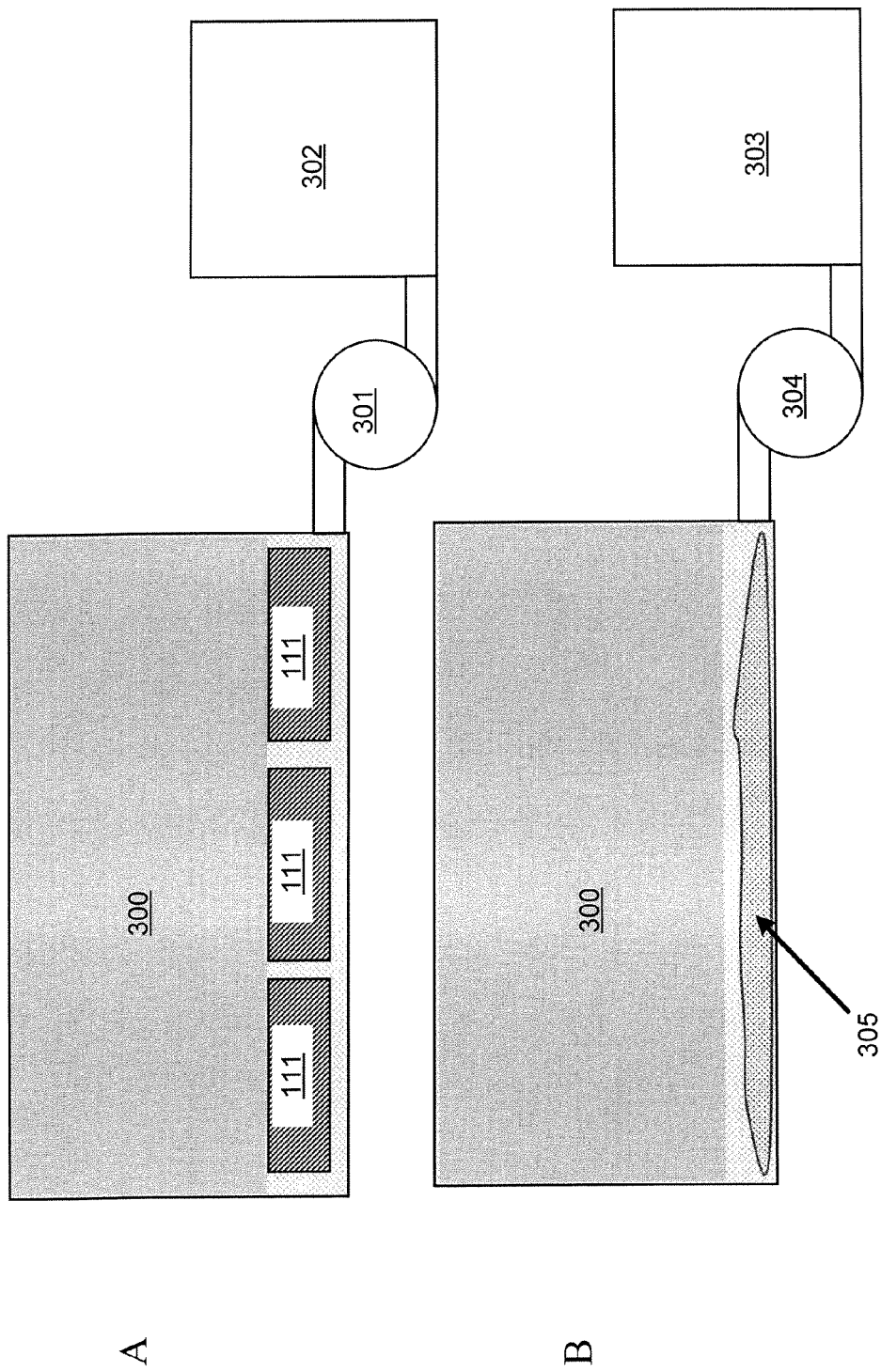
FIG. 3 is a diagram of the filter dissolving and adsorbent regeneration and recovery steps for the process of FIG. 1.

The special adsorbent 102 can be added to the adsorbent filter 111 during manufacture of the filter. In this embodiment, no paddle or stirring device 104 or adsorbent holding tank 103 is needed. The fluid stream 100 is pumped through the filter bank 200 to remove the pollutant by direct contact. If longer residence time in the filter is needed, the pump and plumbing can be modified to allow more filters in the bank in series. The number of filters and the size of the filters are determined by the desired output concentration of the pollutant, the kinetics of adsorption by the adsorbent, the design of the filters, and the flow rate of the process stream through the filters. When the filters have reached the designed capacity of pollutant, the purified stream output valve 109 can be closed and the reverse flow restrictor valve 106 opened. Then the pump 105 back flushes the filters to remove physisorbed contaminant into a holding tank or the input process stream via back flush valve and stream 110. At the same time the valve to operate the parallel adsorbent filter array 200 is opened so the process stream flow is not interrupted. The spent filters may then be removed and disposed as before or sent to the adsorbent recovery process, as shown in FIG. 3.

In an exemplary embodiment, it may be desirable to reclaim the adsorbent from the spent filter. FIG. 3 shows an example of a filter material (matrix) medium from a fiber or material that can be dissolved using a suitable solvent. One nonlimiting examples of such a combination is cellulous acetate that can be dissolved in acetone. In step "A", the adsorbent laden filters 111, 200 can be placed in a reacting tank 300 containing a dissolving solution, thereby dissolving the filter matrix and allowing the adsorbent 305 to collect in the bottom of the reacting tank 300. A pump 301 may be used to pump the dissolving liquid from the reacting tank 300 to the holding tank 302.

As shown in FIG. 3B, the collected adsorbent 305 may still have significant pollutants chemically bound to it. As a non-limiting example, this may be up to approximately 600 mg of mercury (or other contaminant) per gram of adsorbent. This residual pollutant can be removed (thereby regenerating the adsorbent) by using a second reservoir 303 and pumping system 304. A dissolving fluid holding tank (not shown) may be used with this second system, and is not shown in FIG. 3B in order to better illustrate the regeneration step.

In one embodiment, a pump 304 may be used to move an acid solution, such as 1 M HCL, from the holding tank 303 into the filter dissolving tank 300 that contains the recovered adsorbent 305. The strong acid removes the contaminant, such as mercury, from the adsorbent. The acid is then pumped back into the holding tank 303, or if sufficiently spent by previous contact with the process stream 100, it is pumped into a storage tank for subsequent chemical processing and regeneration. The regenerated adsorbent 305 may be collected by various means. For example, it may be collected by draining the filter dissolving tank 300, then filling the tank with washing liquid, such as water, and re-draining. The clean adsorbent 305 may then be dried and collected mechanically. Alternatively, if a magnetic adsorbent is used, the adsorbent may be washed as described above, then collected by a magnetic collection device. An example of such a magnetic collection device is shown in FIG. 4.

In an exemplary embodiment, the adsorbent 305, once collected, is conveyed to the hopper holding the adsorbent 103, as seen in FIG. 1, where it can be combined with new magnetic or non-magnetic support 103 and then added to the adsorption assembly. The magnetic support and adsorbent 305 may be disassociated from the bound contaminant in the regeneration process 300. The magnetic support and adsorbent 305 is re-injected into the contacting tank 103 to remove additional mercury from contaminated liquid 100.

Figure 4:
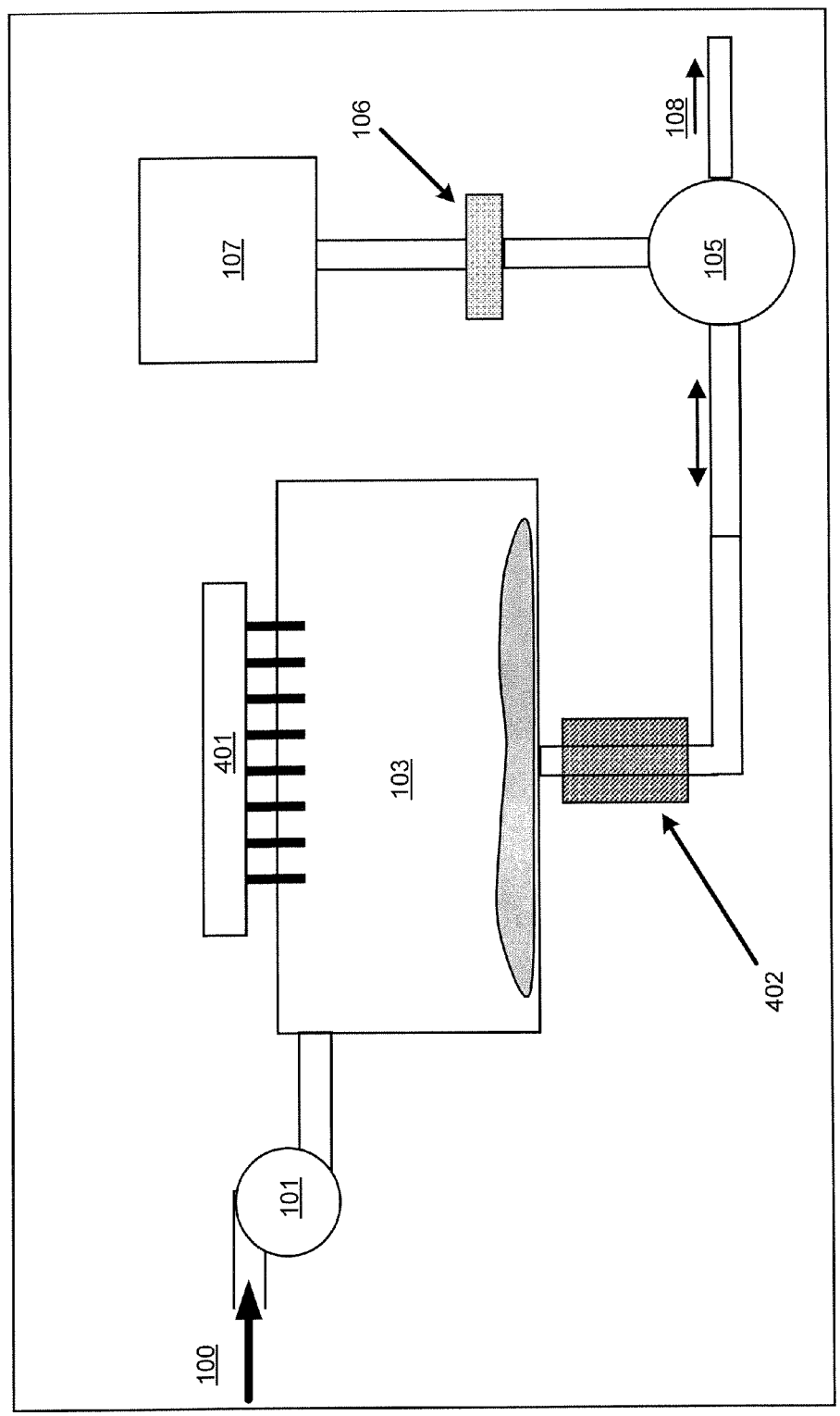
FIG. 4 is a diagram of a magnetic recovery process in accordance with another exemplary embodiment of the present invention.

FIG. 4 shows a schematic diagram of an exemplary magnetic recovery method for the regenerated adsorbent 305. When magnetic supports are used for the adsorbent the use of the adsorbent filter bank 111 is not needed. The system may include a polishing filter 402 that removes particulates that may damage the pump 105. In this example, the adsorbent and magnetic support is added to the adsorbent contacting tank 103 as shown in FIG. 1. After a suitable time, the magnetic separator device 401 is lowered into the tank while the liquid is being re-circulated and the magnetic fields are activated. The magnetic adsorbent particle is attracted to and held by the electromagnetic separator and separated from the purified liquid. At this time, the purified liquid is pumped from the tank by a pump 105 into the next step in the process of disposal.

The adsorbent held by the electromagnetic separator can then be replaced in the adsorbent-liquid contacting tank if it still has capacity to bind the contaminant. If the adsorbent capacity is insufficient, the adsorbent can be moved to the filter dissolving tank and subjected to the regeneration process (see FIG. 3B). After the tank is filled with stripping acid, the adsorbent is added to the liquid by discontinuing the activating electric current to the electromagnets. Once stripping is completed, the adsorbent can be recollected with the magnetic separator, and thereupon re-enter the cycle as new adsorbent 102.

Figure 6B:
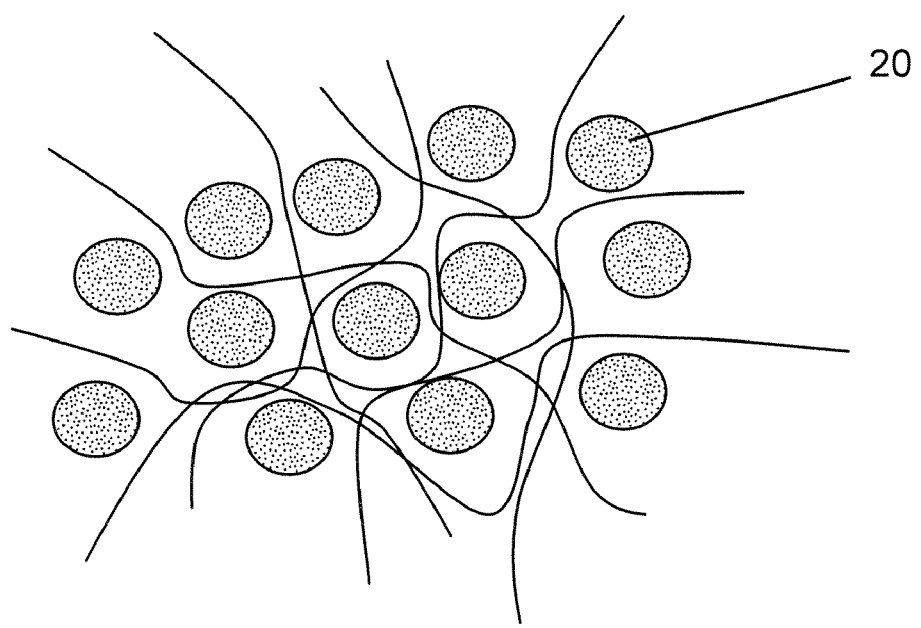
FIG. 6B is a diagram of an adsorbent particle held in a supporting media in accordance with an exemplary embodiment of the present invention.

Referring to FIG. 6, the magnetic support 10 in this exemplary embodiment is a ferrimagnetic material, such as magnetite (ferrous ferrite) or manganese ferrite. The magnetic particles may range in size from about 2 μm to 100 μm, but in one exemplary embodiment preferably are about 2-10 μm. The magnetic particles should be sufficiently small in size to be suspended in the liquid phase of a process system, but not so small that their magnetic moment is reduced so as to interfere with the collection and recirculation system. Very small powder can travel downstream in the process liquid and adversely impair filtration systems or pass through them. The magnetite-type particle of 2 to 10 micrometers may be a secondary particle or aggregate comprised of primary particles of size from 1 to 200 nanometers, with the primary particles sized large enough to achieve sufficient magnetic moment so that they may be collected using magnetic means.

Figure 7A:
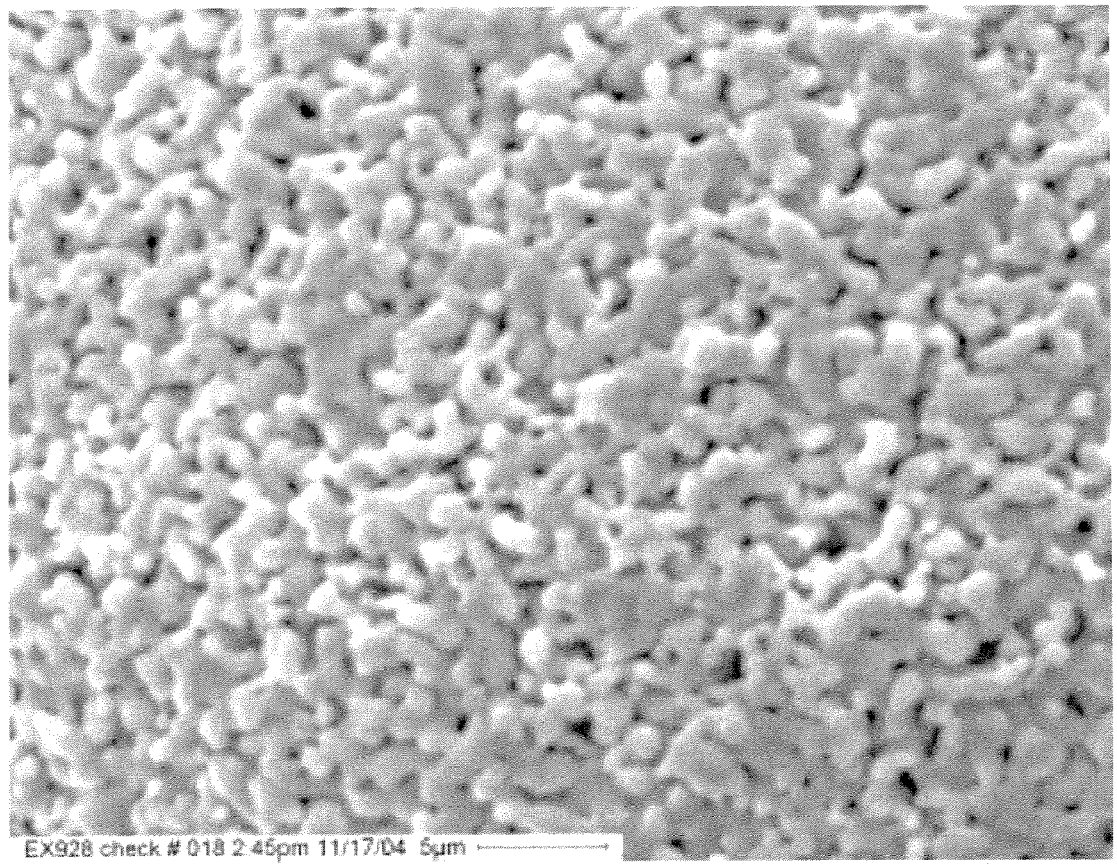
FIG. 7A is a photograph of a plasma-processed Mn—Fe ferrite.
Figure 7B:
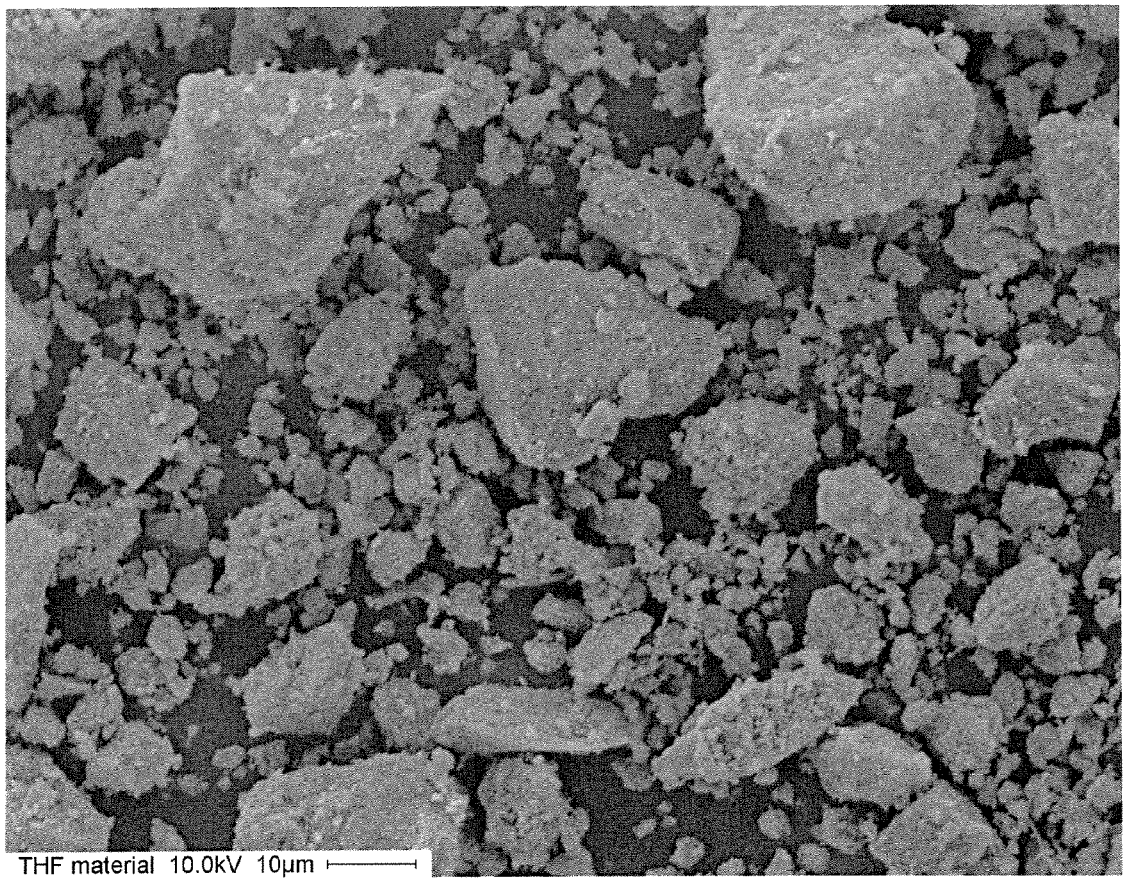
FIG. 7B is a photograph of an adsorbent using magnetite support.

One exemplary form of a magnetic support 10 may be produced as follows: an aqueous slurry of hematite ($d_{50}$ on the order of 2-4 μm) is spray dried into an aggregate (approximately 30-80 μm) and calcined into an easily-handled granular powder. Depending on the specific process steps (e.g., starting milled powder size, time, temperature and atmosphere), a wide range of specific surface area can be created (surface area/unit volume). For purposes of making sintered solids, a surface area of no greater than approximately 0.1-0.6 $m^2/g$ is sought for this embodiment; however, this number can be increased significantly, up to approximately 1-2 $m^2/g$ or even higher. FIG. 7 shows an example of this powder. One method to make a magnetite powder is to use plasma processing. This method allows the production of highly spherical powder in size from the order of dust (approximately 10-100 nm) up to the approximate size of the sintered spray-dried aggregate discussed above.

Another alternative to obtain higher surface area is to obtain magnetite made by chemical precipitation in the form of primary particles in the size range of 1-200 nm. These powders can be carefully spray dried, or otherwise agglomerated and very carefully sintered at low temperature of about 300-400° C. to make aggregates about 1-10 micrometer size. The aggregates serve as a support for the active adsorbent. Another example of a suitable magnetite is the chemically precipitated magnetite such as product 8502 produced by Nanochemonics of Pulaski, Va.

Figure 5:
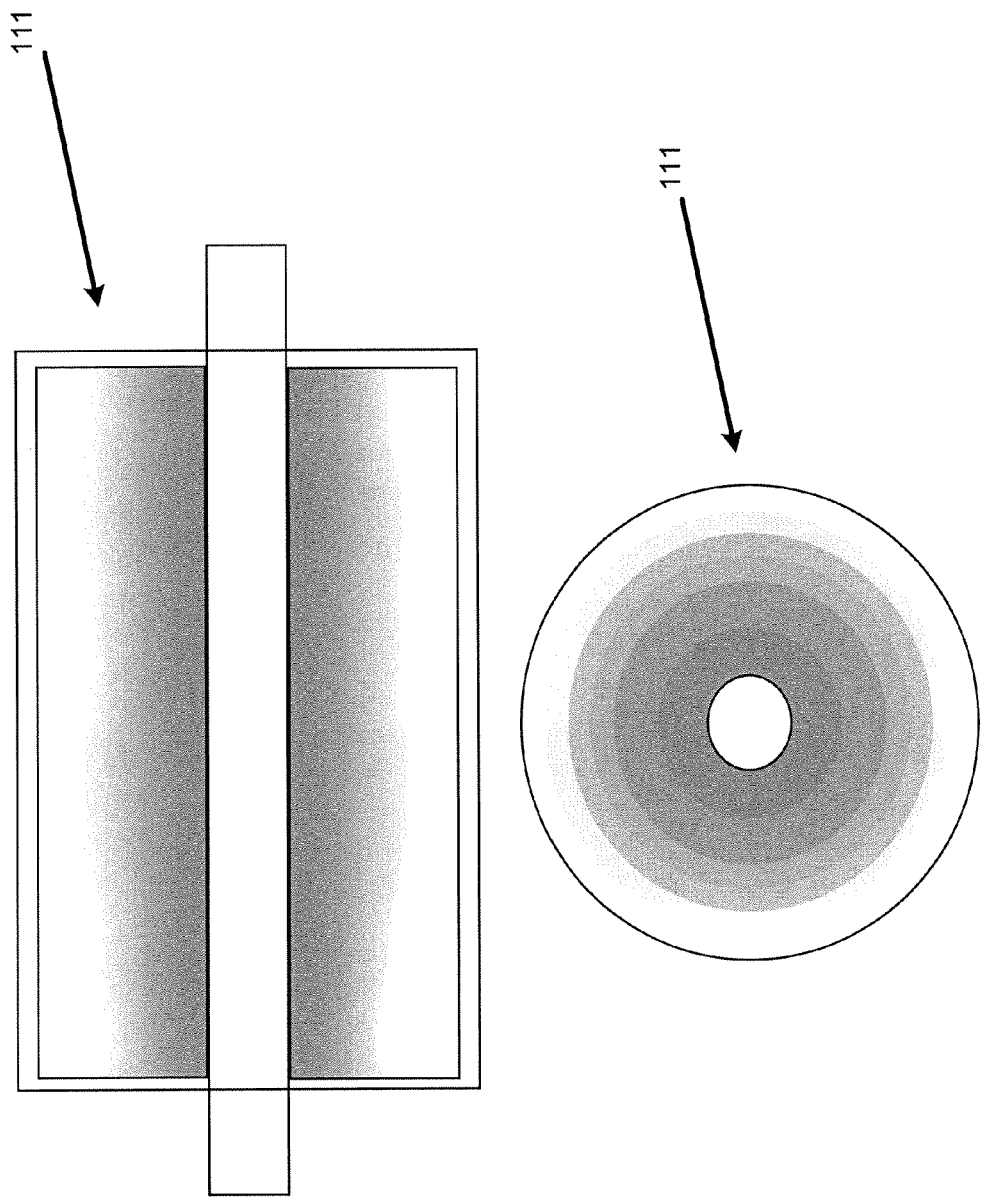
FIG. 5 is a diagram of a filter matrix containing an adsorbent in accordance with an exemplary embodiment of the present invention.

FIG. 5 shows an example of a filter design for filters used as described above to hold adsorbent. The filter 111 may be designed with a gradient in density or porosity, although other density-gradient or uniform density filters may be used. A filter may contain a uniform distribution of adsorbent particles (as described below) and be constructed of a material that is easily dissolved in a specific solvent. The solvent should not be found in the process stream 100. Thus, when such a filter is placed in the filter dissolving tank 300, as shown in FIG. 3, the adsorbent may be recovered. Alternatively, if a suitable density gradient is used in the filter, it will be possible to use a non-magnetic support for the adsorbent, as shown in FIG. 4. The filter will capture the adsorbent as the process liquid is pumped from the tank and when the back-flush operation is conducted the adsorbent will be moved out of the filter and back into the tank. When properly designed the filter will have very high capture efficiency for the adsorbent but upon back flush will release adsorbent back into the contacting tank 103.

The purpose of the matrix is to hold the adsorbent. In this exemplary embodiment, by adjusting the packing and density of the matrix from exterior to center, a gradient of porosity can be achieved which enhances filter performance by trapping larger particles in the outer part and progressively smaller particles in towards the center. This filter is designed not only to remove particulate matter but also to remove the mercury or other heavy metal contaminant. The filter matrix is constructed by mixing the adsorbent in proper particle size and density so as to achieve the desired adsorbent loading. A density gradient is not necessary for adsorbent performance.

In this embodiment, attachment of the sorbent to the filter matrix requires that: (1) it be sufficiently strong to survive the thermal, abrasive and chemical conditions of the process stream; (2) it provide for a high surface area to volume ratio;

and (3) it resist poisoning or degradation of the absorbing or catalytic properties of the sorbent. Any sorbent 5 that is active for the agent can be used.

In an embodiment where mercury is the contaminant of interest, the sorbent is chosen to react with mercury in the liquid process stream. A number of exemplary choices for sorbents are possible. For example, catalysts/adsorbents can be made by attaching mercury-active catalysts to meso-porous silica. Silanols can be attached to silica substrates and achieving higher density of functional sites. U.S. Pat. No. 6,326,326, for example, describes functional groups to bind mercury and describes the phenomenological method. 3-mercapto-propyltrimetoxysilane also may be used to form the adsorbent (the mercapto-group) and the attachment. When the substrate (support) is silica, these monolayer films may reach values of SSA (specific surface area) of approximately 200 $m^2$/g. Older publications show that both an alkylsilizane and an alkylalkoxysilane (the only difference in the two is the nature of the functional group containing the silicon atom used to anchor the silanol) can be attached to the activated surface of Co-γ-$Fe_2O_3$. Alkylsilazane forms Si—O chemisorbed bonds to the oxide, leaving a strongly hydrophobic surface with the alkyl groups aligned normal to the surface. The silazane is a strongly adsorbed, monolayer bound tightly to the substrate. It is superior to the loosely bound alkylalkoxysilane.

The efficiency of a directly functionalized sorbent 5 depends on its placement on a supporting surface of a support 10 that has a high specific surface area (SSA or surface area/unit volume). The SSA of natural magnetite is usually approximately or less than 1 $m^2$/g. The SSA of magnetite converted from hematite depends greatly on the SSA of the hematite and the specific thermal process. Hematite made by converting iron chlorides in pickle liquor has intermediate SSA of approximately 8-10 $m^2$/g, while oxide made from the carbonyl iron process has higher SSA, approaching 18 $m^2$/g. Some chemically converted hematite is reported to have SSA of approximately 50 $m^2$/g. The average diameter of these powders is on the order of 0.3-3 μm. A small powder is hard to handle so it is usually spray dried to larger size and partial sintered at moderately high temperature under low partial pressure or reducing conditions for handling and conversion to magnetite. The SSA of the hematite influences the SSA of the spray dried powder. For example, when a sample of high purity grade hematite is given a thermal treatment in a controlled atmosphere (<1000 ppm $PO_2$ at 800-1000° C.), it is relatively easy to obtain SSA between 1 and 2 $m^2$/g. Other products, such as Magnox MNP-9002 Black Pigment whose primary particle size is approximately 10 nm and has surface area of approximately 100 $m^2$/g, may also be used.

Suitable spray drying and subsequent treatments by calcining (such as making an approximately 50 micrometer diameter spray-dried particle and passing this spray-dried material through a rotary calcining kiln at approximately 400° C.) produces a larger aggregate but preserves surface area at between 75-90 $m^2$/g. This makes an ideal magnetic support having moderately large pores and high surface area.

It should be recognized that a number of prior art methods treat the pyrolysis of the metallo-organic silicon compounds to the ceramic state. Generally these compounds show increasing cross-linking above about 200-300° C., and certainly by 400° C. True conversion to ceramic does not occur until approximately 1000° C. or above. A significant amount of nano-scale free carbon can be produced in these materials, especially with di- and tri-functionalized silizanes with gaseous ammonia. While careful pyrolysis and selection of chemistry of the starting polymer may yield a conversion to ceramic, mesoporous surface. A mesoporous material has pore diameter between 20 to 500 Å.

An alternative method whereby the catalyst is anchored to a ceramic substrate via solution processing and calcining may be used. Prior art methods describe anchored catalysts and adsorbents for removing $SO_X$, $NO_X$ and organic compounds. These include various embodiments of anchored systems using colloidal alumina, silica or metal oxide such as iron oxide as a binder, and another metal oxide as adsorbent or catalyst. Some of these methods permit the achievement of a high specific surface area and also provide much higher site density of adsorbents on such mesoporous silica substrates.

Although hematite is a preferred embodiment for a ferrimagnetic substrate or support, other spinel ferrites with substituted transition metal oxides can be used. For example, MnO can be added to form a Mn—Fe ferrite whose stoichiometric form is give by the formula $MnOFe_2O_3$. NiO also may be added to $Fe_2O_3$ to form nickel oxide spinels. One advantage of adding these ceramic oxides to make an "alloy" consistent in providing a change in the Curie temperature. The Curie temperature of $Fe_3O_4$ is 585° C. and the Curie temperature of $MnFe_2O_4$ is 300° C. Although one might consider a very high Curie temperature to be advantageous, the ability to cause a ferrite to spontaneously lose its magnetization can allow a recovery system where the powder is recovered magnetically and released by heating over its Curie Temperature.

As discussed above, in one exemplary embodiment, after collection in the magnetic separator or regenerators, the oxidized mercury can be disassociated from the sorbent using an acid wash, (e.g., 12 N or 37% (wt.) HCl). Finely divided ferrite is highly reactive in HCl solution. The ferromagnetic material is imparted with surface coverage of silane which provides resistance to dissolution by the acid used to strip the mercury.

The use of a magnetic adsorbent 20 provides a unique advantage by avoiding contaminating the fly ash with mercury when using surface binding methods for adsorbent or catalyst through the use of magnetic separation. In this embodiment, the mercury only need be effectively bound to the ferrite and removed in ESP. Since the ferrite is magnetic, a magnetic separation step applied in collection precipitate removes the mercury-containing ferrite. Magnetic separation is commonly used in the production of substrate beads or electro-photographic copiers. This method would replace an anchored adsorbent or catalyst system with a silylated method.

The degree of wetting by water, also called hydrophilicity (increased wetting), decreases and the degree of repelling water also called hydrophobicity (less wetting) increases. When an aqueous liquid is treated, it is more efficient to have a hydrophilic surface. Conversely, when organic liquids are treated, it is more efficient to have a hydrophobic surface.

As discussed in U.S. Pat. No. 6,326,326, as the degree of surface coverage of the desired silanol adsorbent increases, so does the hydrophobic character of the surface. The binding capacity for mercury increases as the surface area of the particle increases, reaching a theoretical maximum of about two grams of mercury per gram of adsorbent for a support with 900-1000 $m^2$/g. However, the reported measured capacity is shown to be lower, about 0.6 g of mercury per gram of adsorbent. This can be explained by less than full surface coverage and by inefficient use of the pore area of the artificial zeolite. That is, while the average pore size may be 3.5-6 nm, there are many very small pores of small diameter that are too small to be used for adsorbing mercury.

In one embodiment, it is advantageous to use as a support a material such as Sipernat50 made by Degussa. Although this material only has a surface area of 450 m²/g, it has an average pore size of about 20 nm and when functionalized as described herein can exhibit a capacity for mercury adsorption up to 0.7 grams of mercury per gram of adsorbent. Furthermore, the kinetics of adsorption are at least as fast as obtained using a functionalizing procedure to a support such as MCM-41 manufactured by Mobil-Exxon.

Specific examples are described below:

EXAMPLE 1

This example describes the production of a dissolvable and magnetically recoverable adsorbent for mercury. A small quantity of cellulose acetate fiber, 0.5 gram, was dissolved in approximately 20-30 ml of reagent acetone to create the cellulose acetate (CA) dope. Approximately 1 liter of deionized water was placed in a large beaker. A hand-held battery powered laboratory agitator was used to stir the solution. The dope was added to the vortex of the vigorously stirred water dropwise using a small pipette while continuously stirring the water. When all the dope had been added, stirring was stopped and the water allowed to go to a quiescent state.

A layer of CA fiberettes formed in the water and floated as a surface layer on the water. These fiberettes were skimmed off with a laboratory spoon and placed in a 250 mm evaporating dish and as much water-acetone solution as possible was decanted. An additional aliquot of water was added to assist mixing adsorbent in the next step.

A 0.2 g sample of an adsorbent particle comprised of a support of magnetite whose surface was functionalized with 3-mercaptopropyl-trimethoxysilane. The 0.2 g was added to the cellulose acetate fiber mixture and stirred gently until all the adsorbent was uniformly distributed in the CA fiberettes.

This mixture was "cast" into a laboratory syringe body into which previously was added a small layer of glass wool to keep the fibrettes and adsorbent from flowing through the syringe output end. Gentle pressure was applied to the syringe to remove most of the water and reduce the CA/adsorbent mass to a cylindrical volume of about 2.54 cm diameter and 2.54 inch height.

Figure 8:
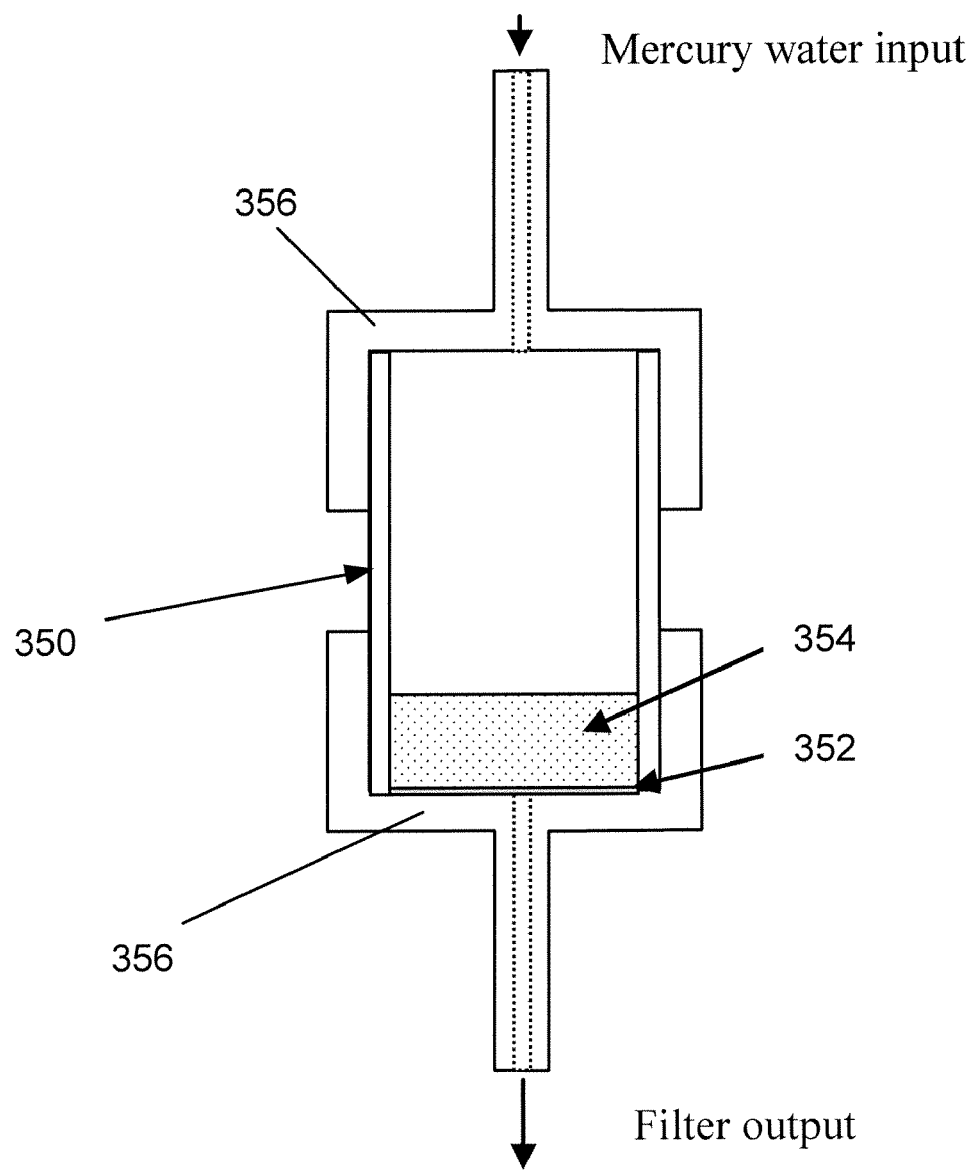
FIG. 8 is a diagram of a fixed bed adsorbent filter in accordance with an exemplary embodiment of the present invention.

As shown in FIG. 8, this adsorbent filter plug was removed from the syringe and placed in a single fixed bed column to make an adsorbent filter 200. The column consisted on a 0.9 inch inside diameter clear PVC pipe 350 with a 60 mesh screen 352 at one end to hold the adsorbent filter plug 354. Both ends of the pipe were fitted with fittings 356 to attach delivery and recovery tubes for mercury water and filtrate water.

The filter was connected to a reservoir containing water of 8.1 ppb (weight) concentration and allowed to flow through the adsorbent filter (approximately 5.2 cc volume) by gravity feed. A flow rate of 12.5 cc/minute was obtained. This is a flow rate of 0.75 gallons/ft² per minute. The dwell time of the liquid in the adsorbent was 25 seconds.

The output of the filter was collected and measured twice in a cold vapor atomic fluorescence unit (Tekran model 2600) showing the concentration was reduced to 0.47 ppb and 0.52 ppb for an average output of 0.5 ppb. This is a 94% reduction in mercury with extremely short contact time. Further reduction could be obtained by increasing the depth of the bed (thickness of the adsorbent filter). A higher flow rate can be accommodated by increasing the area of the filter.

Figure 9:
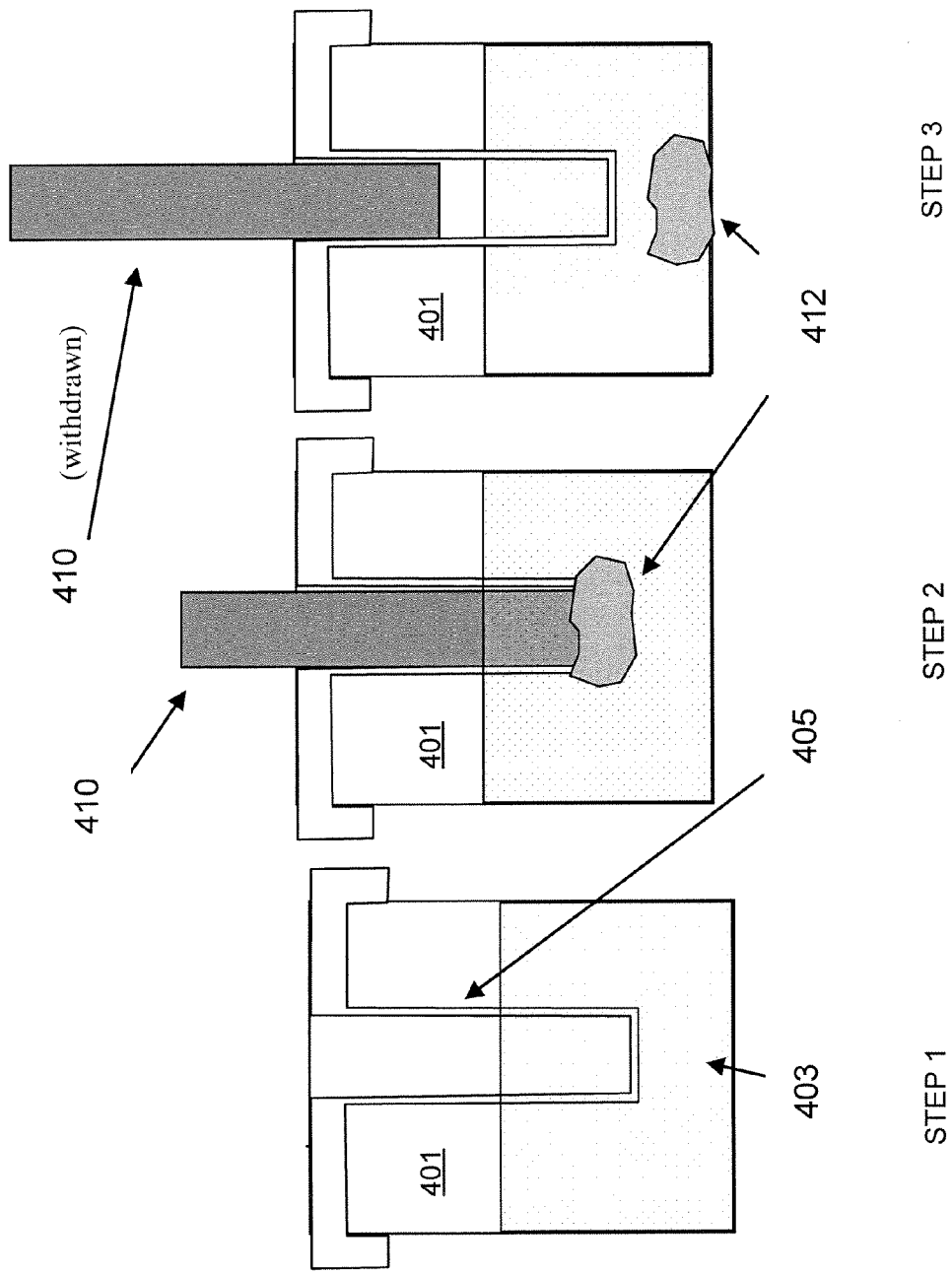
FIG. 9 is a diagram of a magnetic recovery apparatus for removing a pollutant from a liquid in accordance with an exemplary embodiment of the present invention.

When the test was completed, the adsorbent filter was dismantled and the CA filter recovered. It was placed in a container beaker (filter dissolving tank 300) and enough reagent acetone 360 added to dissolve the CA assisted by gently stirring. The ferrite was deposited on the bottom of the beaker. The beaker was vigorously stirred and the contents (CA filter and acetone) 403 transferred to the magnetic separator. As shown in FIG. 9, the separator was stirred and the magnet 410 placed inside the collection arm 405 separating the magnetite adsorbent particles 412 from the liquid to the arm 405. The magnet assembly 410 was removed and placed in a receiving vessel and the magnet removed.

When the magnet 410 was removed from the collection arm 405 the ferrite 412 fell into the receiving vessel 401. A small amount of acetone was used to wash the few adhering magnetite adsorbent particles. All the magnetite in the original CA filter was collected (approximately 0.1 gram) and can now be used again by repeating this process. The cycle can continue until the adsorbent capacity of the adsorbent or a desired output concentration of mercury is reached. It should be evident that the filter described in this example, while used as an adsorbent filter 111, 200, could also serve as a polishing filter 402.

EXAMPLE 2

Figure 10:
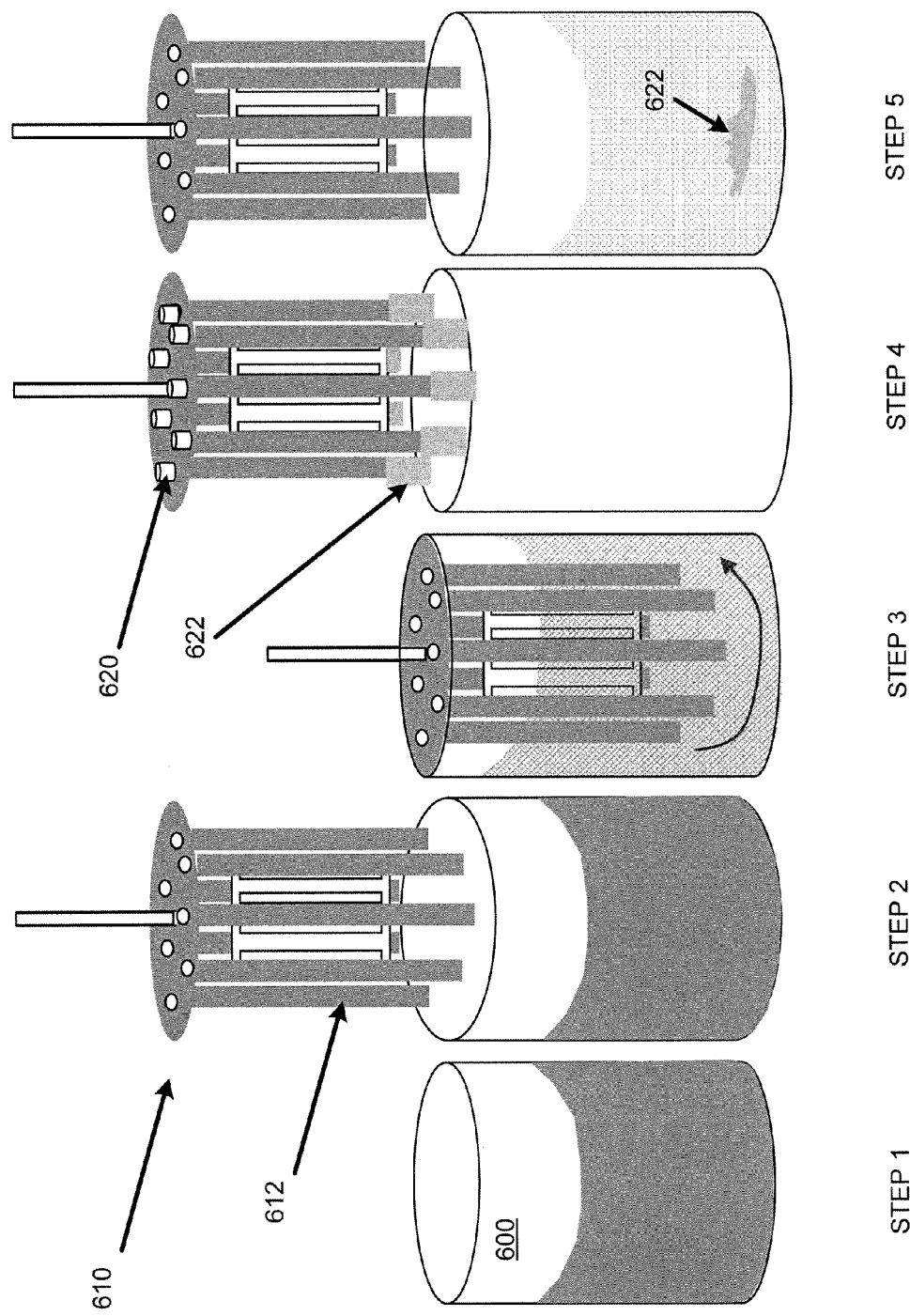
FIG. 10 is a diagram of a batch adsorption process in accordance with an exemplary embodiment of the present invention.

This example addresses how the magnetic recovery process can be combined with a "batch" adsorption process, as shown in FIG. 10. In Step 1, the same magnetic support with adsorbent as used in Example 1 above is added to a reservoir 600 containing approximately 1 liter of liquid holding 30 ppb mercury. The ratio of mass of adsorbent to volume of fluid was 1 gram per 500 ml of liquid.

In Step 2, the stirring assembly 610 with collection arms 612 is inserted into the reservoir 600 holding the adsorbent and liquid. In this case, as shown, the stirring assembly is a rotating turbine stirrer. The magnets or electromagnets used for collection are not inserted or energized.

In Step 3, the reservoir is stirred for a determined period suitable to obtain a desired reduction in mercury concentration.

In Step 4, the magnets 620 are inserted into the collection arms, or the electromagnets are activated, while the solution is stirred. The magnetic force collects the magnetic adsorbent 622 onto the collection arms 612. When the adsorbent 622 is collected on the collection arms, the magnetic assembly is raised from the reservoir and moved to a receiving vessel.

In Step 5, the collection assembly is inserted into the receiving reservoir and the magnets removed or electromagnets de-energized, causing the adsorbent 622 to fall into the vessel where it can be regenerated or reused as in Step 1.

At Step 4, the concentration of the mercury in the liquid in the reservoir was approximately 10 parts per trillion (ppt) by wt. This process was repeated again using new adsorbent and the concentration of the liquid at Step 4 was reduced from 30 ppb to 60 ppt (wt).

Thus, it should be understood that the embodiments and examples have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art. Accordingly, it is intended that the scope of the invention be defined by the claims appended hereto.

We claim:

1. A method to remove a polluting agent from a liquid, comprising the steps of:

placing an adsorbent in contact with the liquid, said adsorbent comprising a sorbent material attached to a support, wherein said support is a filter matrix, under conditions where the polluting agent binds to the adsorbent;

separating the adsorbent from the liquid; and removing the polluting agent from the adsorbent.

2. The method of claim 1, wherein the sorbent is a chemical moity reactive with the polluting agent.

3. The method of claim 1, wherein the sorbent is attached to the support by a strong chemical bond.

4. The method of claim 1, further comprising the step of: reusing the adsorbent.

5. The method of claim 1, wherein adsorbent is suspended in the liquid.

6. The method of claim 1, wherein the filter matrix is soluble in a dissolving agent.

7. The method of claim 6, wherein the adsorbent is not soluble in the dissolving agent.

8. The method of claim 6, further comprising the step of: dissolving the filter matrix so as to recover the adsorbent.

9. The method of claim 1, wherein the support is non-magnetic.

10. The method of claim 1, wherein the support is magnetic.

11. The method of claim 10, wherein the adsorbent with magnetic support is suspended in the liquid in a discrete magnetic containment field.

12. The method of claim 1, wherein the rate of removal of the polluting agent from the liquid is monitored.

* * * * *